United States Patent [19]
Crews et al.

[11] 4,405,719
[45] Sep. 20, 1983

[54] METHOD OF STABILIZING PLATELETS FOR DETERMINING MULTIPLE PLATELET PARAMETERS IN REFERENCE CONTROL AND CALIBRATOR COMPOSITIONS; DILUENTS THEREFOR; AND COMBINATION STABILIZATION PROCEDURES

[75] Inventors: Harold R. Crews, Miami; James H. Carter, II, Ft. Lauderdale; Ted Sena, Miami, all of Fla.

[73] Assignee: Coulter Electronics, Inc., Hialeah, Fla.

[21] Appl. No.: 268,050

[22] Filed: May 29, 1981

[51] Int. Cl.³ .................. C09K 3/00; G01N 33/48
[52] U.S. Cl. .................................. 436/10; 424/101; 435/2; 436/17; 436/18
[58] Field of Search ............ 23/230 B; 252/408; 436/10, 17, 18; 435/2; 424/101

[56] References Cited

U.S. PATENT DOCUMENTS

| | | | |
|---|---|---|---|
| 3,873,467 | 3/1975 | Hunt | 252/408 |
| 3,968,248 | 7/1976 | Boucher | 252/408 |
| 4,102,810 | 7/1978 | Armstrong | 252/408 |
| 4,116,635 | 9/1978 | Jaeger | 252/408 |
| 4,157,383 | 6/1979 | Sedlacek et al. | 252/408 |
| 4,160,644 | 7/1979 | Ryan | 252/408 |
| 4,198,206 | 4/1980 | Ryan | 252/408 |
| 4,213,876 | 7/1980 | Crews et al. | 252/408 |
| 4,299,726 | 11/1981 | Crews et al. | 252/408 |
| 4,302,355 | 11/1981 | Turner, Jr. et al. | 252/408 |
| 4,324,686 | 4/1982 | Mundschenk | 252/408 |

*Primary Examiner*—Teddy S. Gron
*Attorney, Agent, or Firm*—Meredith P. Sparks; Gerald R. Hibnick

[57] ABSTRACT

This invention utilizes for stabilization of platelets a combination of iodoacetamide and an iminodiacetic acid or salt thereof, together with a compatible bacteriostatic agent, in an aqueous electrolytic solution which is maintained at a preselected range of pH and osmolality.

In a preferred formulation, the stabilizing solution contains iodoacetamide, N-(2-acetamido)iminodiacetic acid and sodium penicillin. Ethylenediaminetetraacetic acid, or salts thereof, are optionally present as an additional ingredient.

11 Claims, No Drawings

METHOD OF STABILIZING PLATELETS FOR DETERMINING MULTIPLE PLATELET PARAMETERS IN REFERENCE CONTROL AND CALIBRATOR COMPOSITIONS; DILUENTS THEREFOR; AND COMBINATION STABILIZATION PROCEDURES

BACKGROUND OF THE INVENTION

This invention concerns a method for stabilizing human or animal platelets without the use of aldehydes or other fixative agents for determining multiple platelet parameters in reference controls using electronic instrumentation, as well as diluents therefor. As a result of modern technological advances, instrumentation systems for enumeration of cellular biological components for clinical diagnostic purposes has increased, and this has created a need for improvement of quality control products.

To make the platelet reference controls, the platelets are removed from the blood by centrifugation, washed with buffered saline, and then "fixed" with agents such as glutaraldehyde, formaldehyde, pyruvic aldehyde, or the like. The aldehyde-reacted platelets are then suspended in a buffer.

The suspended platelets are not stable and will aggregate under a number of circumstances. In addition, the aldehyde-reacted platelets gradually change shape, shrinking in size as they age.

The aldehyde-reacted platelets are intended to be used in particle counters which are affected by particle size. Thus, the reference control should ideally contain platelets which are as similar as possible in size to the platelet particles in normal human blood. It is apparent that aggregation will affect the count and size of the particles in the reference controls. It is also apparent that any shrinking or swelling which occurs also will impair the value of the control, since the platelets are no longer the same size as platelets in fresh human blood.

Several human platelet reference controls are currently marketed. However, improvement is needed with respect to long term stability in the measurement of mean platelet volume and size distribution width.

One such instrumentation system is the Coulter® S-Plus hematology system which counts and examines the count and volume distribution of human platelets in whole blood specimens. Similar type instruments are manufactured by other companies for this purpose. Specifications as to electronic calibration are well defined to the operator of such instruments. Any human platelet reference control must satisfy all of the criteria that are measured on human patient specimens. The reference control needs to simulate as closely as possible that of normal fresh whole blood specimens. It must also conform to properly set thresholds as to the count mode, correctly balanced apertures, current, amplification gain settings, and responsiveness of the system as to all functional aspects.

Mean platelet volume distribution analysis has gained recognition recently as a useful measurement for clinical application. Human platelet size distribution width can now be calculated from specifically measured parameters. Each of the measured parameters lends itself to improvement in examining the log normal distribution of human platelets. Also, changes and shifts in the mode result in erroneous counts.

The common cause of count discrepancies is aggregation. Aggregation of platelets creates doublets that count in the white blood cell mode resulting in unreliable quality control measures. To the extent that platelets undergo aggregation, the aggregated platelet cells appear and are counted as white cells on the automated instrument. Since the number of platelets present are about 30 times the number of white cells present in fresh blood, even if only a small percentage of platelets aggregate, this can cause unreliable results with respect to the white cell count, especially after treatment with the usual fixing agents.

The adhesiveness of platelets also leads to false counts. The adhesion of platelets to "foreign" surfaces has been measured by a variety of methods. The principle of all of these tests is the same. The decrease in platelet count which occurs when blood is allowed to contact a "foreign" surface for a standarized period of time is determined. This decrease is indicative, in part, of the number of platelets which have adhered to the foreign surface, and this value, expressed as a percentage of the original platelet count, has been called adhesiveness. However, it is known that some of the loss of platelets is also due to platelet aggregation. Adhesiveness of platelets, although dependent upon either calcium or magnesium ion is not as selective in this regard as the adhesiveness of the polymorphonucleocytes.

Platelets participate in primary hemostasis by forming aggregates at the site of the injured blood vessels. The agent which is ultimately responsible for platelet aggregation is probably adenosine diphosphate (ADP), which may be derived from the injured tissues and erythrocytes or released from the platelets themselves by, among others, collagen, thrombin and epinephrine. In some patients with bleeding disorders, and in normal patients following an ingestion of some drugs, platelet aggregation by one or more of these agents may be impaired. This impairment of platelet aggregation may be the cause of the prolonged bleeding time which is often obtained in these patients.

Another discrepancy in platelet count is brough about by poor performance of stability until the expected expiration date of the control. Attempts to stabilize human platelets have proved to be extremely difficult. One major problem is that of disintegration of the platelet membrane. Fixatives have been used as a source of controlling disintegration. When platelet membranes disintegrate, they cause debris, thereby resulting in erroneous counts. New methods through improved computer technology for curve filling of raw data are beset by these problems.

Our invention discloses a method of processing human or animal platelets and stabilization without the use of fixatives such as glutaraldehyde which lends itself to eliminate the aforementioned discrepancies.

In U.S. Pat. No. 4,198,206 to Ryan (1980), which is a continuation-in-part of U.S. Pat. No. 4,160,644 (1979), a method is described for preparing a control from platelets which do not aggregate, and which have the same size as platelets in human blood, and maintain their size for at least 6 months. This control is a suspension of aldehyde-reacted platelets that have been washed with a solution of (1) an amino acid which is glycine or alanine;
(2) glycol, glycerol or methanol;
(3) sodium chloride and sodium phosphate; and
(4) a solid polyethylene glycol (molecular weight 4000 to 20,000).

The proposed mechanism of this reaction shows that the amino group of the amino acid reacts with the aldehyde group so that further reaction, which includes cross-linking that leads to hardening and shrinking of the platelets, cannot occur.

It is suprising that in the present invention superior results are obtained by utilizing iodoacetamide, which has the formula $ICH_2CONH_2$, and ADA which has the formula $H_2NCOCH_2N(CH_2COOH)_2$, without using aldehyde-treated platelets.

Following the procedure of our invention, the long term stability is increased without changing the size distribution of the cells present. Thus the patient results which are reported to the diagnostic clinician can be assured of correct results. This leads to improved health care and improvements in the health care industry.

SUMMARY OF THE INVENTION

This invention concerns a method for stabilizing human or animal blood platelets without the use of aldehydes or other fixative agents for determining multiple platelet parameters in reference controls using electronic instrumentation. More particularly, this invention provides a novel stabilizing composition for suspending platelets which can act as a control reagent with the capacity of monitoring the desired platelet parameters of a patient's blood sample. These parameters include platelet count, size distribution width, mean platelet volume, and signal/noise ratio (debris), especially in stand alone preparations.

Stabilization of platelets is then brought about by adding to an aqueous electrolyte solution thereof a suitable quantity of a combination of (1) iodoacetamide and (2) an iminodiacetic acid, and the alkali metal and alkaline buffer salts thereof, together with a compatible bacteriostatic agent, while maintaining the solution within a preselected range of pH and osmolality.

The preferred iminodiacetic acid is N-(2-acetamido)iminodiacetic acid (ADA) and the preferred bacteriostatic compound is a member of the penicillin family, especially sodium penicillin, which may have other stabilizing action on the platelets.

Ethylenediaminetetraacetic acid (EDTA), the sodium or potassium salts thereof, or hydroxyethylethylenediamine triacetic acid, may be included in the formulation.

DETAILED DESCRIPTION OF THE INVENTION

This invention utilizes for stabilization of platelets a combination of iodoacetamide and an iminoacetic acid or salt thereof, together with a compatible bacteriostatic agent, in an aqueous electrolytic solution which is maintained at a preselected range of pH and osmolality.

Iodoacetamide acts to reduce or inhibit adhesiveness of platelets and polymorphonuclear cells. Without being limited to any theory of action, it is known that platelets and polymorphonuclear cells have actively glycolyzing systems, and data are consistent with the hypothesis that iodoacetamide acts on the adhesiveness by blocking glycolysis. However, data are likewise consistent with any hypothesis which ascribes the adhesiveness to sulfhydryl dependent mechanisms with similar sensitivities to iodoacetamide.

The adhesiveness of platelets also appears to be dependent upon divalent cations, although the concentration required by the platelets seems to be much lower than that required by polymorphonuclear cells. Both magnesium and calcium ions are required for adhesiveness. Calcium ions alone are unable to restore adhesiveness to polymorphonuclear cells from blood which has been treated with a chelating resin to remove divalent cations.

The combined use of N-(2-acetamido)iminodiacetic acid (ADA) and iodoacetamide has also shown that human platelets can be stabilized for extended periods of time without aggregation or losing their integrity. Iodoacetamide alone does not neutralize these factors. Also, buffering properties are not sufficient for suspending in platelet rich plasma.

When combining iminodiacetic acid salts, especially ADA, with iodoacetamide we improve the stability, eliminate aggregation, and gain the benefits of the anticoagulation properties of ADA. The buffering properties of ADA are ideal for human platelets. Approximately 0.5 g to about 2.0 g of iodoacetamide is added per liter of stabilizing solution.

Suitable iminodiacetic acid compounds are N-(2-acetamido)iminodiacetic acid (ADA), sodium ADA, potassium ADA, lithium ADA, Tris-ADA or imidazole ADA. Approximately 0.5 g to about 2.0 g of ADA, or an equivalent weight of a salt thereof, is added per liter of aqueous suspension of the platelets, for example, to platelet rich plasma.

The compatible bacteriostatic agent includes sodium penicillin G, potassium penicillin G, procaine penicillin G, penicillin V potassium, ampicillin and carbenicillin.

| PREFERRED FORMULATION | |
|---|---|
| 1. Iodoacetamide | 1.0 g |
| 2. N—(2-acetamido)iminodiacetic acid (ADA) | 1.0 g |
| 3. Sodium chloride | 9.4166 g |
| 4. Sodium penicillin | 0.155 g |
| q.s. to 1/Liter with distilled water | |
| Osmolality = 310 | |
| Adjust pH to 7.0 ± 0.1 with NaOH. | |

In the above formulation, it is desirable to add ethylenediaminetetraacetic acid (EDTA), or salts thereof, as an optional ingredient to act as a chelating agent for divalent ions. Approximately 0.5 g to about 2.0 g of EDTA, or an equivalent weight of salt thereof, is added per liter of aqueous suspension of the platelets.

| Method of Preparation |
|---|
| 1. Add approximately 500 ml distilled water to a 1 liter flask. |
| 2. Add ADA 1 g and allow to dissolve. |
| 3. When disodium EDTA is included in the formulation, add 1 g and allow to dissolve. |
| 4. Add iodoacetamide 1 g and allow to dissolve. |
| 5. Add sodium chloride 9.4166 g and allow to dissolve. |
| 6. Add sodium penicillin 0.155 g and allow to dissolve. |
| 7. q.s. with distilled water to 1 liter. |
| 8. Adjust pH to 7.0 ± 0.5 with sodium hydroxide, and osmolality of 330 ± 30 with sodium chloride. |
| 9. Filter through 0.22 micron filter into sterile bags. |
| 10. Store at room temperature up to six months. |

Jaeger U.S. Pat. No. 4,116,635 studied the anticoagulant properties of both EDTA and ADA using whole blood, and reported the results in TABLE I of his patent specification. Log K', which is the conditional stability constant at pH of 7.5, was found to be 7.9 for EDTA and only 4.0 for ADA. In a process for testing a sample of blood for coagulation and other factors according to his claim 1, the anticoagulent selected had a Log K' from 3.4 to about 4.2, thus including ADA, but excluding EDTA.

It is surprising that, in our invention, best results are obtained when both ADA and EDTA are used together in approximately equal amounts in the formulation. The amount of EDTA which is added to the aqueous formulation of platelets is approximately 0.5 g to about 2.0 g per liter.

The following examples illustrate the method of stabilizing blood platelets without the use of fixative agents for determining multiple platelet parameters by electronic instrumentation.

| STABILITY OF PLATELET RICH PLASMA WITHOUT TREATMENT WITH STABILIZING SOLUTION | | |
|---|---|---|
| Time | S/N | MPV |
| initial | 5.55 | 6.6u |
| after 4 days | 5.00 | 6.6u |
| after 4 days | 2.08 | 6.1u |
| after 6 days | 1.82 | 6.0u |
| after 7 days | 1.43 | no fit |

The above results were obtained when stabilizing solution was stored at 2° to 8° C. and assayed on a standard Coulter ® S-Plus instrument.

The signal/noise A/N ratio decreased with time, i.e., the noise increased relative to the signal. All parameters exhibited changes with time. After seven days, complete cellular fragmentation was demonstrated, resulting in a no-fit mode of the distribution analysis chart. The platelet count, mean platelet volume (MPV), and size distribution could not be determined by the instrument.

Representative samples of glutaraldehyde fixed platelets in phosphate buffered saline solution likewise show a decrease in mean platelet volume over a period of time. Currently manufactured clinical hematological instrumentation cannot tolerate a shift to the left (decrease) of the mean platelet size distribution. This shift results in a no-fit condition.

Excessive debris produces no-fit in size distribution curves.

| REPRESENTATIVE SAMPLES AFTER TREATMENT OF PLATELETS WITH STABILIZING SOLUTION HAVING THE PREFERRED FORMULATION | | | | |
|---|---|---|---|---|
| Day No. | S/N | Count | Mean Platelet Vol. | Mean Size Distribution |
| 30 | 4.54 | 206 | 7.8 | 17.1 |
| 60 | 4.0 | 202 | 7.9 | 17.1 |
| 90 | 4.0 | 193 | 7.6 | 17.1 |
| 120 | 4.0 | 206 | 7.7 | 17.2 |
| 180 | 4.0 | 193 | 7.6 | 17.1 |

The above results were obtained when stored at 2° to 8° C. and assayed on a standard Coulter ® S-Plus instrument. These results show that there is no significant change in any of the parameters after 180 days. There is excellent stability with respect to all critical parameters necessary for quality control applications measured by electronic devices.

Signal/noise ratios must be maximized to assure the operator that the instrument is performing according to the manufacturer's specifications. Increased noise has been an ever present problem because of platelet debris and cellular fragmentation during the life of such products. In these samples, the signal/noise ratio shows no decrease, which would render the instrument incapable of critically measuring parameters for quality control measures. Decreased signal/noise ratios of electronic particle sizing devices, especially in the lower thresholds where platelets are counted and their size distribution determined, cannot be tolerated.

Statistical data documents the use of the above stabilized human platelets in a whole blood control preparation beyond 100 days in several clinical hematology laboratories.

Preconditioning human platelets with the stabilizing solution of this invention allows the cells to be resuspended into a human or animal red blood cell preparation as a control for monitoring electronic devices. Also, it is possible to stabilize human platelets for in vitro therapeutic applications.

For preconditioning the platelets, approximately 50 to 100 ml of the stabilizing diluent is added directly to a 200±50 g unit of platelet rich plasma (PRP) and mixed well. The stabilized PRP can then stand at room temperature for 7 days before centrifugation for procurement of platelet concentrate. In the alternative, the PRP with addition of stabilizing diluent may be stored at 4° to 6° C. for up to 3 months before processing by centrifugation to harvest the platelet concentrate.

PRP is centrifuged at approximately 3,800 RPM for 5 minutes (refrigerated centrifuge) and the supernate is expressed off to waste. Phosphate buffered saline at pH 7.0 to 7.2 and 320 mOs/kg is added with mixing and the washing step is repeated a second time. The platelets are concentrated after the second wash and pooled into a single high concentration pool.

The platelet concentrate is resuspended in the diluent at the desired concentration, and this preparation is added to stabilized erythrocytes to be utilized as a whole blood control. The final preparation is stored at 2° to 8° C. for up to 6 months.

This diluent successfully stabilizes platelet rich plasma procured with the use of commonly utilized anticoagulents such as CPD (citrate-phosphate-dextrose), ACD (acid-citrate-dextrose) and EDTA (ethylenediaminetetraacetic acid).

The stabilized platelets can be utilized in stand alone platelet controls, as well as in whole blood reference controls, to assure good quality control procedures and monitor multiple platelet parameters including (1) count, (2) mean size distribution, (3) mean platelet volume, and (4) signal/noise ratio (debris).

It is well recognized in the art that stabilized blood cell preparations useful for checking the accuracy of automatic counting instruments for blood components are subject to some degree of acceptable variation. Such preparations are discussed briefly on page 14 of the book HEMATOLOGY, by Williams, Beutler, Erslev, and Rundles, McGraw-Hill, Inc. (1972).

In the art of hematology, a difference is made between the terms "calibrator" and "reference control". Calibrators are blood cell preparations that are used to set the automated instrument with respect to certain key numbers, and are used only once. Reference controls are blood cell preparations used from time to time to check the continuing accuracy of an automated instrument which has previously been "calibrated" with the calibrator blood cell preparation.

It is an advantage of this invention that platelets which have been stabilized by the methods herein described, without the use of aldehydes as fixing agents to give reference controls which are stable for 60 days and longer, can then be subjected to a second stabilization treatment by other methods, including methods employing aldehydes and/or surfactants to give platelet preparations having improved stability over a longer period of time, especially for certain purposes. Such preparations are particularly useful in calibrator compositions.

For example, the platelets stabilized by the preferred formulation of this invention can then be treated with a fixative-stabilizer media having the following formulation:

| | |
|---|---|
| $NaH_2PO_4 \cdot H_2O$ | 0.196 g |
| $Na_2HPO_4 \cdot 7H_2O$ | 0.980 g |
| $NaN_3$ | 0.098 g |
| NaCl | 7.9 g |
| Glutaraldehyde, 49% | 8.4 g |
| Tergitol ® 15-S-12 | 0.5 g |
| Water q.s. | 1 L |
| Adjust to pH 7.3 to 7.4 with phosphate, and to an osmolality of 290 mOs/kg with NaCl. | |

Tergitol ® 15-S-12 is a mixture of ethoxylates of isomeric linear alcohols, as described in U.S. Pat. No. 3,912,450 (1975) and U.S. Pat. No. 3,968,248 (1976), Boucher to Wave Energy Systems, Inc., and sold as Wavecide-01. The mixture has the formula:

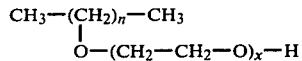

in which the polyoxyethylene chain is randomly attached to the linear aliphatic chain, wherein n=9 to 13 and x=9 to 13.

The resulting platelets are useful in calibrators. The above described fixative-stabilizer media is described further and claimed in co-pending application, Ser. No. 06/268,049 filed May 29, 1981.

We claim:

1. A method for long term stabilization of blood platelets without the use of aldehydes or other cross-linking fixative agents for use in determining multiple platelet parameters in reference controls for electronic instrumentation, which method comprises adding to platelets in a suspending fluid a stabilizing solution which is an aqueous solution of:
   (1) iodoacetamide in a concentration of approximately 0.5 to 2.0 g per liter; and
   (2) one or more compounds selected from the group consisting of an iminodiacetic acid in a concentration of approximately 0.5 to 2.0 g per liter, and an equivalent weight of an alkali metal or alkaline buffer salt thereof, wherein the resultant media is maintained at a preselected range of pH and osmolality.

2. The method of claim 1 wherein said iminodiacetic acid is N-(2-acetamido)iminodiacetic acid.

3. The method of claim 1 wherein a bacteriostatic agent which is a member of the penicillin family consisting essentially of penicillin G, potassium penicillin G, procaine penicillin G, penicillin V potassium, ampicillin and carbenicillin is present as an additional ingredient.

4. The method of claim 1 wherein ethylenediaminetetraacetic acid, the sodium or potassium salts thereof, is present as an additional ingredient.

5. The method of claim 4 wherein said ethylenediaminetetraacetic acid is present in a concentration of 0.5 g to 2.0 g per liter.

6. The method of claim 1 wherein said stabilizing solution is added directly to freshly collected platelet rich plasma.

7. The method of claim 1 wherein said stabilizing solution is added to platelet rich plasma for procurement of platelet concentrate by centrifugation.

8. The method of claim 1 wherein the final pH is adjusted to 7.0±0.5.

9. The method of claim 1 wherein the osmolality is adjusted to 330±30 milliosmoles using sodium chloride.

10. A hematology reference control media for determining multiple platelet parameters utilizing electronic instrumentation comprising a suspension of platelets which is stabilized by adding a stabilizing solution which is an aqueous solution of:
    (1) iodoacetamide in a concentration of approximately 0.5 to 2.0 g per liter.
    (2) one or more compounds selected from the group consisting of an iminodiacetic acid in a concentration of approximately 0.5 to 2.0 g per liter, and an equivalent weight of an alkali metal or alkaline buffer salt thereof, wherein the resultant media is maintained at a preselected range of pH and osmolality.

11. A multiple analysis hematology reference control comprising a suspension of stabilized red blood cells, together with platelets stabilized without the use of aldehydes or other fixing agents by adding to said platelets in a suspending fluid a stabilizing solution which is an aqueous solution of:
    (1) iodoacetamide in a concentration of approximately 0.5 to 2.0 g per liter.
    (2) one or more compounds selected from the group consisting of an iminodiacetic acid in a concentration of approximately 0.5 to 2.0 g per liter, and an equivalent weight of an alkali metal or alkaline buffer salt thereof, wherein the resultant media is maintained at a preselected range of pH and osmolality;
    wherein said control is capable of being used for testing the accuracy and precision of whole blood controls and multiple platelet parameters.

* * * * *